United States Patent [19]

Meijer

[11] Patent Number: 5,165,873
[45] Date of Patent: Nov. 24, 1992

[54] TWO-CYCLE PERISTALTIC PUMP

[75] Inventor: Robert S. Meijer, San Diego, Calif.

[73] Assignee: IMED Corporation, San Diego, Calif.

[21] Appl. No.: 840,667

[22] Filed: Feb. 20, 1992

Related U.S. Application Data

[63] Continuation of Ser. No. 577,081, Aug. 31, 1990, abandoned, which is a continuation of Ser. No. 419,193, Oct. 10, 1989, abandoned.

[51] Int. Cl.⁵ .............................................. F04B 43/12
[52] U.S. Cl. ........................................ 417/474; 417/479
[58] Field of Search ............ 417/53, 474, 475, 478, 417/479; 604/153

[56] References Cited

U.S. PATENT DOCUMENTS

| | | | |
|---|---|---|---|
| 4,039,269 | 8/1977 | Pickering | 417/475 |
| 4,199,307 | 4/1980 | Jassawalla | 417/474 |
| 4,236,880 | 12/1980 | Archibald | 417/479 X |
| 4,273,121 | 6/1981 | Jassawalla | 417/474 X |
| 4,382,753 | 5/1983 | Archibald | 417/479 |
| 4,479,797 | 10/1984 | Kabayashi et al. | 417/474 X |
| 4,586,882 | 5/1986 | Tseng | 417/477 |
| 4,650,469 | 3/1987 | Berg et al. | 417/474 X |
| 4,657,490 | 4/1987 | Abbott | 417/479 X |
| 4,840,542 | 6/1989 | Abbott | 417/479 X |
| 4,846,637 | 7/1989 | Alderson et al. | 417/474 X |
| 5,017,059 | 5/1991 | Davis | 417/474 |

FOREIGN PATENT DOCUMENTS

| | | |
|---|---|---|
| 0090440 | 5/1983 | European Pat. Off. . |
| 2005269 | 8/1971 | Fed. Rep. of Germany . |
| 3413437 | 4/1985 | Fed. Rep. of Germany ...... 417/474 |

Primary Examiner—Leonard E. Smith
Attorney, Agent, or Firm—Nydegger & Associates

[57] ABSTRACT

A device for pumping fluid through a resilient tube has a platen for holding the tube and a pumping mechanism for squeezing the tube against the platen. The pumping mechanism includes a first pumping finger which squeezes the tube at a first location and a second pumping finger which squeezes the tube at a second location. For their respective alternating pumping actions, the first finger is configured and operated to displace approximately twice the fluid volume displaced by the second pumping finger. A valve means is also mounted on the base and is positioned to alternately occlude the tube upstream from the first and second pumping fingers during the pumping action of the first pumping finger and to occlude the tube between the first and second locations upstream from the second pumping finger during the pumping action of the second pumping finger.

10 Claims, 2 Drawing Sheets

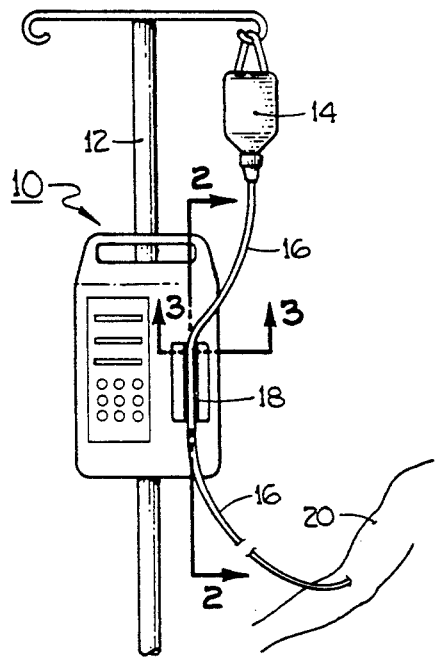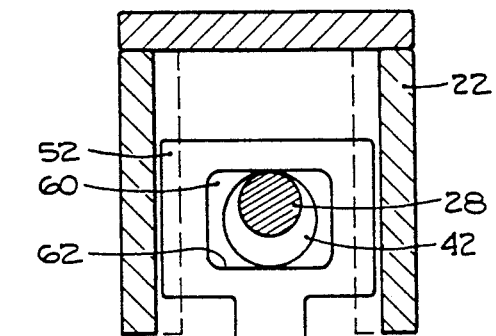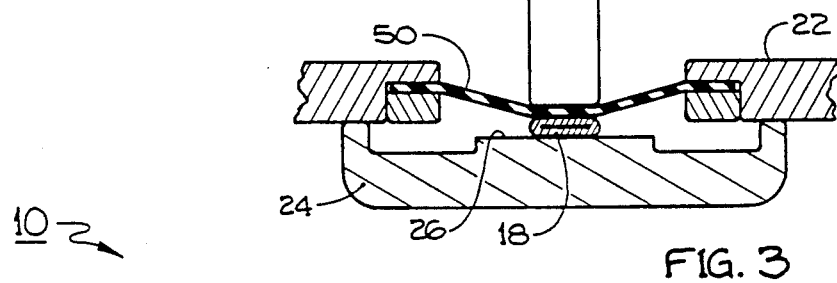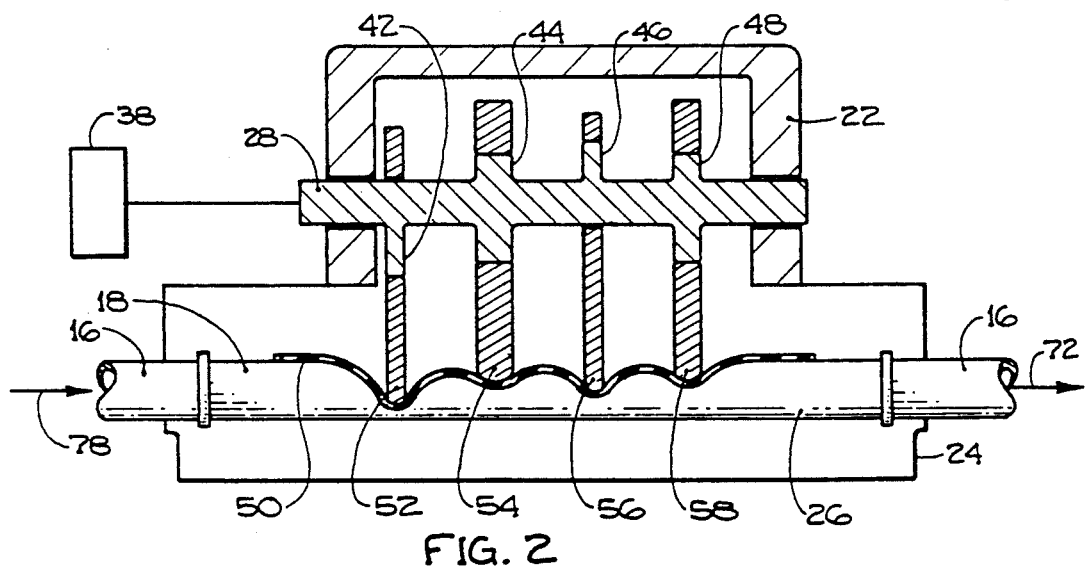
FIG. 1
FIG. 3
FIG. 2

TWO-CYCLE PERISTALTIC PUMP

This is a continuation of co-pending application Ser. No. 577,081, filed on Aug. 31, 1990, now abandoned, which is a continuation of co-pending application Ser. No. 419,193, filed Oct. 10, 1989, now abandoned.

FIELD OF THE INVENTION

The present invention pertains to fluid pumps. More specifically, the present invention pertains to peristaltic pumps which sequentially squeeze a resilient tube to force fluid through the tube. The present invention is particularly, but not exclusively, useful as a pump for the infusion of medical solutions to a patient.

BACKGROUND OF THE INVENTION

Over the years there have been a number of pumps developed for infusion of medical solutions to patients. Such pumping of fluids has been routinely accomplished through a wide variety of well known pumping mechanisms. In the administration of fluids to a patient, it is desirable that the pump be of the "non-wetting" variety, such as that exemplified by the well known peristaltic pump. A peristaltic pump is a type of pump which uses wave-like motion against the walls of a flexible tube containing the fluid being pumped. The non-wetting-type pump is particularly useful in hospital and medical situations in that the fluid being pumped is not subject to contamination through direct contact with the component parts of the pump. In like fashion, if corrosive fluids are being pumped there is no direct contact of corrosive fluid with component parts of the pump.

Another desirable characteristic of pumping mechanisms in general is for the pump to deliver fluid at a rate which remains reasonably constant. In other words, throughout the pumping cycle, the rate of flow should remain even, without any surges or significant variations in the flow rate.

Peristaltic pumps of the non-wetting variety are basically one of two types, namely rotary peristaltic pumps and linear peristaltic pumps. A disadvantage of rotary peristaltic pumps, however, is that they have relatively poor efficiency. In addition, they impose high shear and tension stresses on the tubing which is used to convey the fluid. Another disadvantage is that because of the high forces typically produced by rotary peristaltic pumps, the tubing eventually experiences spalling of its inner walls. There is also, after a period of time, permanent plastic deformation, or "set", of the tubing. In other words, its normally circular cross section becomes flattened into a more oval shape.

Linear peristaltic pumps, in comparison, typically use reciprocating parts to provide peristaltic action against the flexible tube in order to move the fluid through the tube. Such peristaltic pumps consist of a plurality of reciprocating pumping fingers, typically twelve (12), that are sequentially urged against the tube to occlude adjacent segments of tubing in wave-like action. Although linear peristaltic pumps overcome some of the above-stated disadvantages associated with rotary peristaltic pumps, they do so at considerable added cost and with the greater complexity added by the mechanism needed to properly synchronize twelve (12) pumping fingers. Since the pumping fingers are urged to sequentially occlude adjacent segments of tubing, the crushing forces imposed on the tubing and fluid are comparable to those encountered with rotary peristaltic pumps. There is less damage, however, than that caused by rotary peristaltic pumps, since the occlusion forces are localized to the area beneath each finger rather than being applied in movement along the whole length of the tubing. Nonetheless, even with a linear peristaltic pump, there is still some damage such as plastic deformation of the tubing. As a consequence, the structural integrity of the tube carrying the fluid is compromised and as the tubing assumes a progressively more oval cross-sectional shape, the volume and flow rate of the fluid delivered in each pumping cycle is affected.

Furthermore, in order to smooth the pumping transition from one cycle to the next, some linear peristaltic pumps have what is called a "wrap" cycle. During a "wrap" cycle, the motor driving the pump is accelerated to quickly move the upstream finger into occlusion. Thereafter, the motor can resume normal speed to sequentially squeeze and occlude adjacent portions of the tube in its wave-like cycle action. Incorporating this "wrap" cycle can require use of a relatively large and expensive motor with high acceleration capability. Also, because fluid is not delivered during this "wrap" cycle, most linear peristaltic pumps use many fingers (e.g. twelve (12) additional pumping fingers, as mentioned earlier) to minimize the proportionate time of the "wrap" cycle. Maintaining proper alignment and relational movement between such a plurality of fingers also deteriorates the reliability of operation of the device and increases manufacturing costs.

Accordingly, it is an object of the present invention to provide a peristaltic pump of the non-wetting type which is simple and efficient in operation. It is another object of the present invention to provide a peristaltic pump which results in reduced stresses on the fluid-carrying tube and thus longer tube life. It is yet another object of the present invention to provide a peristaltic pump which produces a substantially linear, and non-pulsatile flow for the fluid being pumped. Still another object of the present invention is to provide a peristaltic pump which is relatively easy to manufacture, durable and reliable in its operation and comparatively cost-effective.

SUMMARY OF THE INVENTION

A preferred embodiment of the peristaltic pump for pumping fluid through a resilient tube comprises a base, a platen mounted on the base for holding the tube, and four (4) fingers mounted on the base engageable with the tube. The four (4) fingers include, in sequence downstream, a first pinching finger, a first pumping finger, a second pinching finger, and a second pumping finger. The fingers are mounted reciprocally on the base to urge against the tube between a withdrawn position and an extended position. The first pumping finger squeezes the tube to displace a fluid volume which is approximately twice the fluid volume displaced by the second pumping finger.

A drive mechanism moves the first pumping finger toward its extended position as the second pumping finger is moved toward its withdrawn position. The drive means further moves the first pumping finger toward its withdrawn position as the second pumping finger is moved toward its extended position. The first pinching finger occludes the tube upstream from the first pumping finger as the first pumping finger moves toward its extended position. The second pinching finger occludes the tube between the first and second pumping fingers, as the second finger moves toward its extended position.

In one embodiment, the first pumping finger displaces twice the fluid as a result of its being twice as large as the second pumping finger. In another embodiment, the first pumping finger displaces twice the fluid by traveling a distance which is approximately twice that of the distance traveled by the second pumping finger.

Also disclosed is a method for pumping fluid through the tube which comprises the steps of alternately squeezing the tube at a first and second location corresponding to the point of contact of the first and second pumping fingers. The tube is then alternately occluded or pinched at a point upstream from the first location, and at a point between the first and second locations. The tube is squeezed at the first location when the tube is occluded upstream from the first location by the first pinching finger. The tube is squeezed at the second location while the tube is occluded between the first and second locations by the second pinching finger.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a perspective view of the peristaltic pump in its intended environment;

FIG. 2 is a side cross-sectional view of the peristaltic pump apparatus taken along the line 2—2 of FIG. 1;

FIG. 3 is an end cross-sectional view of the peristaltic pump apparatus taken along the line 3—3 of FIG. 1;

DETAILED DESCRIPTION OF THE PREFERRED EMBODIMENTS

Figure 4:
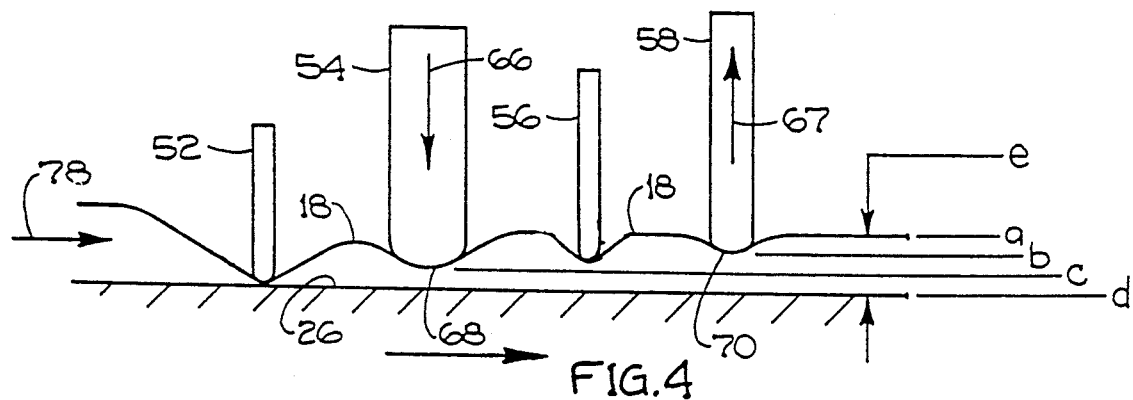
FIG. 4 is a schematic illustration of operation of the peristaltic pump shown in FIG. 1.

Referring now to FIG. 1, there is shown a peristaltic pump apparatus, generally designated 10, shown in use in its intended environment. In particular, peristaltic pump apparatus 10 is shown attached to an intravenous (I.V.) pole 12. Attached to pole 12 is a fluid source 14 containing an I.V. fluid. Fluid source 14 is connected in fluid communication with a hollow resilient tube 16. Tube 16 is a conventional I.V. infusion-type tube for use in a hospital or medical environment, but could likewise be any type of flexible tubing, such as rubber. There is a portion 18 of flexible tube 16 which is mounted in pumping apparatus 10, for pumping fluid through tube 16 into a patient's arm 20.

The components of peristaltic pump apparatus 10 can be best appreciated now with reference to FIGS. 2 and 3. Peristaltic pump apparatus 10 comprises a casing 22 having a base 24 which includes a generally flat platen 26. Platen 26 provides a surface against which tube 18 may be occluded in the manner as shown in FIG. 3.

Mounted in casing 22 is a rotatable shaft 28, which is driven by a motor 38. Motor 38 is a variable speed motor which provides the driving power for driving the pump shaft 28. Shaft 28 is rotatably mounted in casing 22. Shaft 28 also includes cam lobe portions 42, 44, 46 and 48.

Four (4) fingers 52, 54, 56 and 58 are reciprocally mounted in casing 22 onto base 24. Fingers 52, 54, 56 and 58 are reciprocally mounted for being urged against tube 18. To provide further protection for tube 18, and to keep dirt and other unwanted materials from the inner workings of the peristaltic pump 10, a flexible membrane 50 is connected to base 24. Each finger 52, 54, 56, 58 is reciprocally mounted to move up and down with respect to platen 26. Each finger 52, 54, 56, 58 is movable between a withdrawn position, or upper limit, and an extended position, or lower limit, to deform tube 18 a specified amount as explained hereinafter.

In particular, pinching fingers 52 and 56 are of identical configuration, and serve as pinch valves. Fingers 52 and 56 are movable between a withdrawn position as shown by finger 56 in FIG. 2, and an extended position as shown by finger 52 also in FIG. 2. This is also further shown with reference to FIG. 3. As can be seen, rotation of shaft 28 causes corresponding rotation of cam lobe portion 42. Shaft 28 and cam lobe 42 thus rotate within orifice 60 of first pinching finger 52. Cam lobe 42 thus engages a side wall 62 of orifice 60 so as to urge pinching finger 52 to its fully extended position. This causes finger 52 to press against membrane 50 and to urge against tube 18 so as to occlude tube 18 as shown in FIGS. 2 and 3. These fingers are thus positioned so that the smallest possible motion of fingers 52, 56 suffices to alternately occlude or open tube 18 to allow fluid to flow beneath them. In other words, in an open or fully withdrawn position, as shown by finger 56 in FIG. 2, an aperture is provided in tube 18 which is sufficient for relatively unrestricted flow of fluid beneath finger 56 at the maximum rate of the pump. Typically, the extent of the range of motion of pinching fingers 52 and 56 is fixed at no more than one (1) to three (3) times the wall thickness of the tube 18. Thus, first finger 52 and third finger 56 are essentially pinching fingers.

It may also be readily appreciated with reference to FIGS. 2 and 4 that second finger 54 and fourth finger 58 are pumping fingers in the sense that it is these fingers which squeeze tube 18 to urge fluid out of tube portion 18. In addition, first pumping finger 54 has a unique configuration and is designated as a "large" pumping finger. Finger 58 is also of a unique configuration and designated as a "small" pumping finger. With respect to the description of the invention herein, "large" and "small" describe pumping fingers which are constructed to move against tube 18 such that the amount of fluid displaced as "large" finger 54 moves downward against tube 18, is approximately two (2) times that displaced by an equal reciprocal downward motion of "small" finger 58. It is important to note that the reciprocal motion of fingers 54 and 58 is generally equal in range, but that in the fully extended position, the pumping fingers 54, 58 do not ever fully occlude the tubing. Instead, they squeeze the flexible tubing 18 from a relatively larger percent of initial tubing outside diameter to a relatively smaller percent of initial tubing outside diameter.

Figure 5:
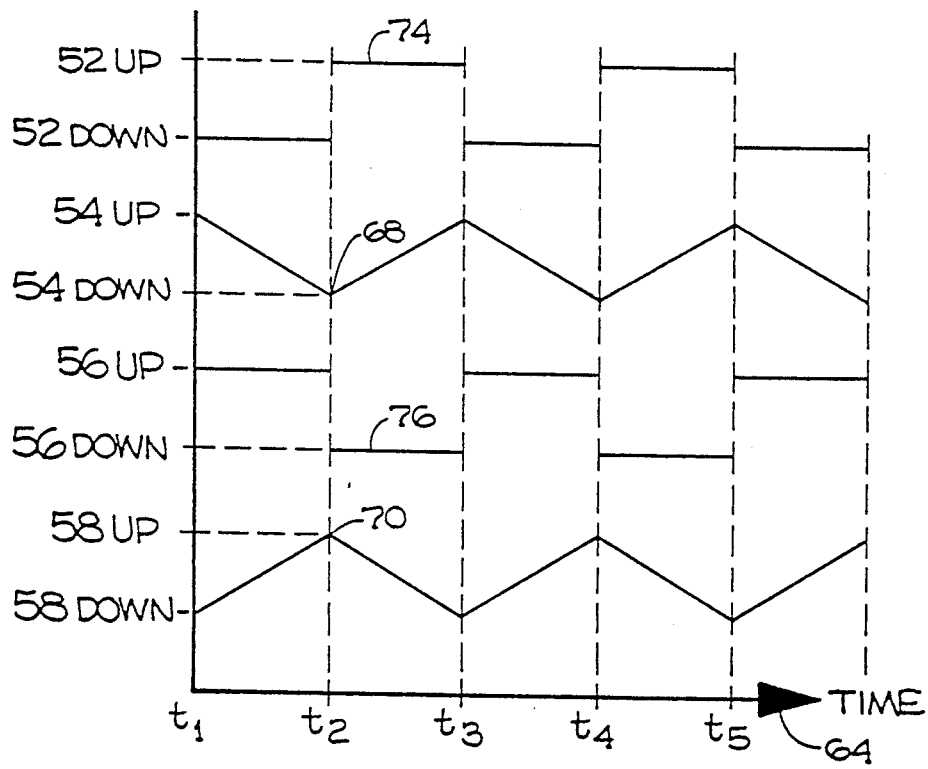
FIG. 5 is a schematic diagram illustrating the relative operation of the movement of fingers utilized in operation of the peristaltic pump in accordance with the present invention.

Operation of the present invention may perhaps be best appreciated with reference to FIGS. 4 and 5. In particular, FIG. 4 represents relative movement of fingers 52, 54, 56 and 58. In FIG. 5, the relative movement of pinching fingers 52 and 56 and pumping fingers 54 and 58 are shown in relation to one another over a period of time that includes reference points $t_1$, $t_2$, $t_3$, $t_4$ and $t_5$ on time line 64. As shown in FIGS. 4 and 5, motor 38 drives shaft 28 and cam lobe 42, 44, 46 and 48 so that fingers 52, 54, 56 and 58 are reciprocated to execute in the present embodiment a two-cycle motion as described below. The first cycle is between time $t_1$ and $t_2$, and the second cycle is between $t_2$ and $t_3$.

In the first cycle, finger 52 is held closed in its fully extended position, while finger 56 is held in its fully withdrawn or open position, as shown in FIG. 4. This is indicated in FIG. 5 on time line 64 at starting point time $t_1$. At point $t_2$ as shown in FIG. 5, finger 52 is in the down position and finger 56 is in the up position. As the motor 38 rotates shaft 28, cam lobes 42, 44, 46 and 48 cause fingers 52 and 56 to remain in the same position, but also cause fingers 54 and 58 to move. Finger 54 moves down in the direction as shown by arrow 66 having started at upper limit or height elevation "b" and moving down to lower limit or elevation "c". Thus, in FIG. 4, finger 54 is shown at its position 68, and is shown in FIG. 5 where finger 54 is in a fully extended position, yet not occluding tube 18. Thus, immediately prior to $t_2$, finger 52 is still down. At the same time, finger 58 which started in its down position at elevation "c" at time $t_1$ has moved up as shown by arrow 67 to position 70 immediately prior to time $t_2$. Thus, finger 54 having moved downward from its extreme retracted position at elevation "b" toward platen 26 drives fluid out and toward patient 20 generally in the direction of exit arrow 72. Simultaneously, finger 58 has started moving upward from its extreme extended position, as shown in the graph on FIG. 5 between time $t_1$ and $t_2$. The difference in the size of the fingers, i.e. "large" versus "small" results in a net delivery of fluid comparable to that resulting from the displacement produced by the "small" finger acting alone. In other words, since the "large" finger 54 displaces twice the volume as that of "small" finger 58, the net result of cycle one is the delivery of one unit of volume toward the exit of tube 16 as shown by arrow 72.

As cycle one is concluding at time $t_2$, the "large" finger 54 and "small" finger 58 have exchanged vertical positions. Also at time $t_2$, pinching fingers 52 and 56 exchange positions. Pinching finger 52 is raised toward its fully withdrawn position as shown at elevation point "c", and pinching finger 56 is lowered as shown by elevation line "d". Since pinching finger 56 is now closed, and pinching finger 52 is open, fluid is drawn into the tubing 16, and thus, portion 18 as shown by entry arrow 78. The rate of flow of fluid into the entrance of tube 18 is twice that of the output rate, since finger 54 displaces twice as much fluid as finger 58. Then, while finger 54 is retracting between time $t_2$ and $t_3$, finger 58 is extending from elevation "b" to elevation "c" as shown in FIG. 4. This produces a net delivery output of one unit of fluid via exit arrow 72.

This action progresses until time $t_3$ at which time cycle two has been completed. At time $t_3$, the pinching fingers 52, 56 again revert so that pinching finger 52 is again down and pinching finger 56 is again up so that they are essentially in position 68 at point in time $t_1$. The system at point $t_3$ is then in the same state it was at time $t_1$. Times $t_4$ and $t_5$ are merely repetitions of an additional cycle.

It is important to note that the speed with which the pumping fingers move toward the tubing during a cycle ideally is not constant. As the tubing is squeezed, equal increments of motion result in a displacement of progressively larger amounts of fluid. In other words, linear reciprocal motion of the finger against the tube as the tube becomes more compressed results in faster flow of fluid out from under the deformed tubing. To accommodate this, the ideal motion of pumping fingers 54 and 58 is such that each finger moves toward the tubing at a relatively rapid pace and then progressively slows as the tubing becomes more deformed. The benefit of such motion is a uniform rate of fluid flow forced by the squeezing action of the respective fingers. Thus, the pumping mechanism having two cycles as described herein is a highly efficient apparatus for effecting fluid displacement. It also provides a linear, non-pulsatile flow of fluid which is desired in peristaltic pumping apparatus. In addition, this design thus allows the use of much smaller motors than would be necessary with either conventional linear or rotary peristaltic pumps. Since the size of the motor required generally reflects the peak rather than the average load encountered, this mechanism redistributes the load reflected so that the motor has a reduced peak. Further, the required occlusion is produced by two small pinching fingers that do not displace significant amounts of volume or distort the metering portion of the tubing. On the other hand, the pumping fingers, unlike conventional peristaltic fingers, never completely occlude the tubing or "crush" the tubing to produce undesired results.

It is also important to note that the present invention avoids waste of energy in linear and rotary peristaltic conventional pumps. The great bulk of such motive energy is typically consumed in heating the tubing through the high compressive and shear forces applied. This is because, as mentioned earlier, the fingers must not only pump but also occlude the tube. The present invention, however, separates the functions of pumping and occluding. Thus, the present invention has removed the need for such repeated mashing and deformation of tubing to occlude it by the pumping aspect. In particular, the plastic set, or deformation, from repeated smashing of tubing does not affect the accuracy of the present apparatus. Any "set" around the area beneath the pinching fingers 52, 56 is much narrower since such fingers are much narrower and have the specific function of occluding the tube. However, the wider area under the wider pumping fingers 54 and 58 do not significantly experience the "set" phenomenon since they are not required to fully occlude the tubing. In other words, the pumping fingers 54, 58 have an upper and lower pumping finger limit as shown by the dimensions "b" and "c" in FIG. 4. The pinching fingers 52 and 56, however, have a shorter motion to fully occlude the inside diameter "e" of the tube between finger heights "a" and the platen height "d".

Figure 6:
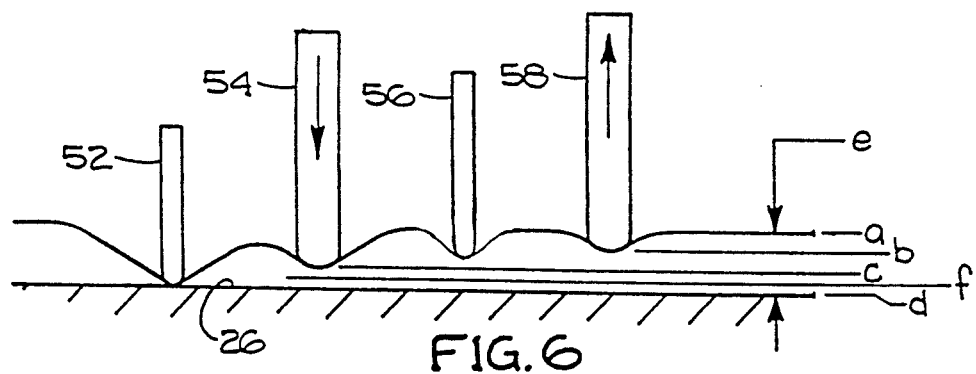
FIG. 6 is a schematic illustration of an alternative embodiment of the peristaltic pump in accordance with the present invention.

Finally, with reference to FIG. 6, there is shown an alternative embodiment representative of the present invention in which pumping fingers 54 and 58 are of identical size. The cam lobes 42 on shaft 28, however, are arranged such that the pumping fingers 54 and 58, being of the same size, are directed through a different amount of travel, respectively. In particular, it can be seen that while the limited travel of reciprocation of finger 58 is between elevations "b" and "c" as shown in FIG. 6, the limited travel of reciprocation of finger 54 is between "b" and "f". The distance between "b" and "f" is a larger distance and thus there is a larger amount of travel. Provided such travel is accomplished during the same period of time, finger 54 thus displaces more fluid.

By properly choosing the amount of travel and deformation of tubing involved, the amount of travel can thus be adjusted so that finger 54 squeezes tube 18 to displace a fluid volume that is approximately twice the fluid volume displaced by the squeezing movement of finger 58.

While the particular two-cycle peristaltic pump as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. A device for pumping fluid through a conventional resilient I.V. delivery tube which comprises:
   a base;
   a platen mounted on said base for holding said conventional tube;
   means mounted on said base for alternately squeezing said tube against said platen at a first location and at a second location, said squeezing means comprising a first pumping finger reciprocally mounted on said base to continuously urge against said tube partially occluding said tube initially at a relatively rapid pace and then progressively slower as said tube becomes more deformed to uniformly displace fluid at said first location and a second pumping finger reciprocally mounted on said base to continuously urge against said tube partially occluding said tube initially at a relatively rapid pace and then progressively slower as said tube becomes more deformed to uniformly displace fluid at said second location partially occluding said tube at said first location; and
   means mounted on said base and synchronized with said squeezing means comprising a first pinching finger reciprocally mounted on said base for alternately occluding said tube upstream from said first location and between said first and second locations, said first location being squeezed as said tube is occluded upstream from said first location with said first and second pumping fingers shaped to urge against a relatively larger area than said first pinching finger.

2. A device for pumping fluid through a resilient tube as recited in claim 1 wherein said first pumping finger contacts an area of said tube that is approximately twice as large as the area of said tube contacted by said second pumping finger.

3. A device for pumping fluid through a resilient tube as recited in claim 1 wherein said second location is squeezed as said tube is occluded between said first and second locations.

4. A device for pumping fluid through a resilient tube as recited in claim 1 wherein between their respective withdrawn and extended positions, said first pumping finger travels a distance which is approximately twice the distance traveled by said second pumping finger.

5. A device for pumping fluid through a resilient tube as recited in claim 4 wherein said tube remains open at said first location and at said second location.

6. A device for pumping fluid through a resilient tube as recited in claim 5 wherein said tube has a lumen with a selected inner diameter and said distances traveled by said first pumping finger and said second pumping finger between their respective said withdrawn position and said extended position is less than said selected inner diameter.

7. A device for pumping fluid through a conventional resilient I.V. delivery tube which comprises:
   a base;
   a platen mounted on said base and adapted to hold said conventional tube;
   a first pumping finger reciprocally mounted on said base to urge against and deform said tube with movement between a withdrawn position and an extended position with movement in the extended position at a relatively rapid pace and then progressively slower as the tubing becomes deformed;
   a second pumping finger reciprocally mounted on said base to urge against and deform said tube with movement between a withdrawn position and an extended position with movement in the extended position at a relatively rapid pace and then progressively slower as the tubing becomes deformed, said first pumping finger partially occluding said tube to uniformly displace a fluid volume that is approximately twice the fluid volume uniformly displaced by the partially occluding movement of said second pumping finger;
   means for moving said first pumping finger toward its said extended position as said second pumping finger is moved toward its said withdrawn position and moving said first finger toward its said withdrawn position as said second finger is moved toward its said extended position including a shaft having first and second eccentric cam lobe portions to engage first and second orifices formed on said first and second pumping fingers respectively;
   a first valve including a first pinching finger slidably and reciprocally mounted on said base for movement over a range of motion of from one to three times a wall thickness of said tube by a third eccentric cam lobe portion on said shaft which contacts a third orifice on said first pinching finger for occluding said tube upstream from said first pumping finger as said first pumping finger moves toward its extended position;
   a second valve including a second pinching finger reciprocally mounted on said base for movement over a range of motion of from one to three times a wall thickness of said tube by a fourth eccentric cam lobe portion on said shaft which contacts a fourth orifice on said second pinching finger for occluding said tube between said first and second pumping fingers as said second finger moves toward its extended position with said first and second pinching fingers contacting a relatively smaller area of said I.V. delivery tube than said first and second pumping fingers; and
   a flexible membrane attached to the base between said tube and said first and second pumping fingers and said first and second pinching fingers.

8. A device for pumping fluid through a resilient tube as recited in claim 7 wherein said first pumping finger is approximately twice as large as said second pumping finger.

9. A device for pumping fluid through a resilient tube as recited in claim 7 wherein between their respective withdrawn and extended positions, said first pumping finger travels a distance which is approximately twice the distance traveled by said second pumping finger.

10. A device for pumping fluid through a resilient tube as recited in claim 7 wherein said tube has a lumen with a selected inner diameter and said distances traveled by said first pumping finger and said second pumping finger between their respective said withdrawn position and said extended position is less than said selected inner diameter.

* * * * *